United States Patent [19]

Baasner et al.

[11] Patent Number: 4,558,166

[45] Date of Patent: Dec. 10, 1985

[54] PROCESS FOR THE PREPARATION OF BENZAL CHLORIDES

[75] Inventors: Bernd Baasner, Leverkusen; Erich Klauke, Odenthal, both of Fed. Rep. of Germany

[73] Assignee: Bayer Aktiengesellschaft, Leverkusen, Fed. Rep. of Germany

[21] Appl. No.: 591,666

[22] Filed: Mar. 21, 1984

[30] Foreign Application Priority Data

Mar. 25, 1983 [DE] Fed. Rep. of Germany ....... 3310953

[51] Int. Cl.$^4$ .............................................. C07C 17/00
[52] U.S. Cl. ...................................... 570/144; 570/191; 570/204; 260/465 G; 568/647; 568/655; 568/656; 568/928; 568/931; 568/933; 568/936; 568/937; 568/635
[58] Field of Search ....................... 570/191, 144, 204; 260/465 G; 568/655, 656, 936, 937, 634, 635, 933, 931, 928, 647

[56] References Cited

U.S. PATENT DOCUMENTS 2,486,542 11/1949 Weisler et al. ...................... 585/469
2,886,605 5/1959 McClure et al. ..................... 585/469

FOREIGN PATENT DOCUMENTS 2139779 12/1972 Fed. Rep. of Germany .
1551559 11/1968 France .

OTHER PUBLICATIONS

Izvestiya Akademi Nauk SSSR, Seria Khimicheskaya, No. 7, 1970 (englische Übersetzung) R. G. Petrova und R. Kh. Freidlina, "The Reduction of α,α,α,ω-tetrachloroalkanes by the Action of Thiols in the Presence of Iron Compounds", Seiten 1438–1485, *Conclusions*.
Tetrahedron Letters, No. 48, 1968, London, I. M. Downie und J. B. Lee, "Reduction of Perhalocompounds with Tertiary Phosphines and Phosphorous Tris(di-n-alkyl) Amides", Seiten 4951, 4952, *Gesamt*.
Patents Abstracts of Japan, unexamined applications, Sektion C, Band 2, No. 140, Nov. 18, 1978, The Patent Office Japanese Government, Seite 3092 C 78 *Kohai–No. 53–105 403 (Sagami Chuo Kagaku Kenkyosho)*.
Cesare Ferri, "Reaktionen in der Organischen Synthese", 1978, Georg Thieme Verlag, Stuttgart, Seite 111 *Reaktion (1)*.

*Primary Examiner*—Charles F. Warren
*Assistant Examiner*—Joseph A. Boska
*Attorney, Agent, or Firm*—Sprung Horn Kramer & Woods

[57] ABSTRACT

Process for the preparation of benzal chlorides from benzotrichlorides, according to which benzotrichlorides are reacted with thiols in the presence of metal salts at elevated temperatures.

11 Claims, No Drawings

PROCESS FOR THE PREPARATION OF BENZAL CHLORIDES

The present invention relates to a process for the preparation of benzal chlorides from benzotrichlorides.

Benzal chlorides are important intermediates which, for example, can be converted into the corresponding benzaldehydes by hydrolysis. Benzaldehydes are used, for example, for the preparation of herbicides (see U.S. Pat. No. 4,212,998 and U.S. Pat. No. 4,212,999).

It is already known that benzotrichlorides can be converted into benzal chlorides. For example, benzotrichloride can be reacted with trivalent phosphorus compounds to give benzal chloride. Good results are obtained in this reaction only in particular cases, for example if phosphorous acid tri-(di-N-ethyl)-amide in ether is used as the trivalent phosphorus compound and the reaction is carried out in the presence of ethanol (see I. M. Downie and J. B. Lee, Tetrahedron Letters 1968, 4951).

$CCl_3$ groups bonded to aliphatics can be reacted with nickel tetracarbonyl in tetrahydrofuran to give $CHCl_2$ groups. However, this process cannot be applied to $CCl_3$ groups bonded to aromatics, since no benzal chlorides are formed and dehalogenating dimerization takes place, diphenylethane derivatives being formed (see T. Kunieda et al., J.C.S.Chem.Comm. 1972, 885).

Another process for converting $CCl_3$ groups bonded to aliphatics into $CHCl_2$ groups uses thiols as reducing agents and is carried out in the presence of iron carbonyls or iron chlorides (see R. G. Petrova and R. Kh. Freidlina, Izvest.Akad.Nauk. SSSR 1970, 1483 (English)). It is not known whether this process can be applied to $CCl_3$ groups bonded to aromatics. In this case also, it must be expected that if $CCl_3$ groups bonded to aromatics are used, diphenylethane derivatives are formed and/or Friedel-Crafts reactions take place.

A process has now been found for the preparation of benzal chlorides from benzotrichlorides, which is characterized in that benzotrichlorides are reacted with thiols in the presence of metal salts at elevated temperatures.

The most diverse benzotrichlorides are suitable for use in the process according to the invention. The starting material can be unsubstituted benzotrichloride ($C_6H_5CCl_3$), or benzotrichlorides which are mono- or poly-substituted on the aromatic nucleus.

Examples of suitable benzotrichlorides are those which correspond to the formula

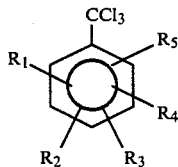

(I)

in which $R_1$ to $R_5$ independently of one another represent hydrogen, nitro, halogen, alkyl, fluoroalkyl, aryl, substituted aryl, O-alkyl, O-fluoroalkyl, phenoxy, substituted phenoxy and/or cyanide.

Halogen radicals here are preferably fluorine and chlorine. Alkyl, fluoroalkyl, O-alkyl and O-fluoroalkyl radicals here preferably contain 1 to 12 C atoms, particularly preferably 1 to 4 C atoms. Aryl, substituted aryl, phenoxy and substituted phenoxy radicals here preferably contain 6 to 10 C atoms, particularly preferably 6 to 8 C atoms. Substituted aryl and substituted phenoxy are preferably alkyl- or nitro-substituted aryl and alkyl- or nitro-substituted phenoxy whereby methyl is the particularly preferred alkyl substituent.

Unsubstituted benzotrichloride or benzotrichlorides which are mono-, di- or tri-substituted on the aromatic nucleus are preferably used in the process according to the invention. Examples of preferred benzotrichlorides are those which correspond to the formula

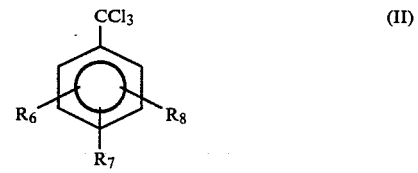

(II)

in which
$R_6$ to $R_8$ independently of one another represent hydrogen, nitro, fluorine, chlorine, cyanide, $C_1$–$C_4$-alkyl, $C_1$–$C_4$-fluoroalkyl and/or O-$C_1$–$C_4$-fluoroalkyl.

Benzotrichlorides of the formula (II) in which $R_6$ to $R_8$ independently of one another represent hydrogen, nitro, fluorine, chlorine, cyanide, methyl, trifluoromethyl and/or o-trifluoromethyl are particularly preferably used in the process according to the invention.

Benzotrichloride, o-chlorobenzotrichloride, p-chlorobenzotrichloride, o,p-dichlorobenzotrichloride, m-fluorobenzotrichloride, p-fluorobenzotrichloride, o-fluoro-o'-chlorobenzotrichloride, o,o'-difluorobenzotrichloride, m-methylbenzotrichloride, o-trifluoromethylbenzotrichloride, m-trifluoromethylbenzotrichloride, p-trifluoromethylbenzotrichloride, m-trifluormethoxybenzotrichloride, o-chloro-m-trifluoromethylbenzotrichloride, m-nitro-m'-trifluoromethyl-p-chlorobenzotrichloride, o-cyanobenzotrichloride, m-cyanobenzotrichloride and p-cyanobenzotrichloride.

The most diverse thiols are suitable for use in the process according to the invention. Thiols which are liquid under the reaction conditions are preferably employed. Other thiols must be used in dissolved form. Aliphatic thiols with 4 or more C atoms and aromatic thiols with 6 or more C atoms are preferably used, for example aliphatic thiols with 4 to 10 C atoms or aromatic thiols with 6 to 8 C atoms. The use of butanethiol and thiophenol is particularly preferred. The use of thiophenol is very particularly preferred.

2 moles of thiol are required for converting 1 mole of a benzotrichloride into the corresponding benzal chloride. 2 moles of a thiol per mole of a benzotrichloride are therefore preferably used in the process according to the invention, since virtually no unreacted benzotrichloride or unreacted thiol then has to be separated off from the reaction mixture. However, the process according to the invention can also be carried out with molar ratios of benzotrichlorides to thiols of less than or more than 1:2.

The process according to the invention is carried out in the presence of metal salts. The metal salts can be of the most diverse type, for example they can also be metal complexes. The reaction is preferably carried out in the presence of salts of sub-group elements. Copper salts and iron salts, for example copper halides and iron halides, are particularly preferred. Of the copper salts, those in which copper is in the +1 oxidation stage are preferred. The use of copper-I bromide is very particularly preferred.

It is sufficient for small amounts of the metal salts to be present. Examples of suitable amounts are those from 0.01 to 10% by weight, those from 0.1 to 5% by weight are preferred and those from 0.5 to 2% by weight are particularly preferred, in each case based on the benzotrichloride employed.

The process according to the invention is in general carried out in the absence of solvents. However, it can also be carried out in the presence of solvents. The presence of solvents is necessary, for example, if thiols which are not liquid under the reaction conditions are to be used. Examples of suitable solvents are those which have a melting point below 80° C. and a boiling point above 100° C., are sufficiently inert and have an adequate dissolving power for the particular benzotrichloride and/or thiol employed. In general, toluene, xylene, mesitylene and methylcyclohexane are particularly suitable solvents.

Hydrogen chloride is split off during the reaction according to the invention. The lower temperature limit for the process according to the invention is therefore the temperature at which the evolution of hydrogen chloride starts in the particular case. In general, this temperature is about 80° C., but in particular cases it can also be higher or lower, for example in the range from 50° to 120° C. The upper temperature limit for the process according to the invention is less critical. From practical considerations, the maximum temperature at which the reaction is carried out is in general the temperature at which the reaction mixture boils under reflux, it being possible for this temperature to be influenced, for example by appropriate choice of the thiol employed, a solvent and/or the pressure in the reaction vessel. The process according to the invention is preferably carried out at temperatures in the range from 50° to 150° C., particularly preferably at temperatures in the range from 80° to 120° C. For example, a procedure may be followed in which the reaction mixture is first heated to 80° C. and the temperature is then slowly increased to 120° C. and kept at 120° C. until the evolution of hydrogen chloride has ended.

The process according to the invention is in general carried out under normal pressure. It can also be carried out under increased or reduced pressure, for example in the pressure range from 0.5 to 20 bar. It may be advantageous to carry out the reaction under a reduced pressure if splitting off and removal of the hydrogen chloride is to be facilitated. Increased pressure may be advantageous if the reaction is to be carried out at temperatures above the boiling point of the component of the reaction mixture which has the lowest boiling point under normal pressure.

The reaction mixture is in general kept at the reaction temperature until the evolution of hydrogen chloride has ended. This time can be, for example, in the range from 2 to 15 hours, and is usually in the range from 5 to 10 hours.

When the reaction has ended, the reaction mixture can be worked up, for example, by distillation. A procedure can be followed here, in which, if a solvent is present, this is separated off and the resulting benzal chloride is removed from the reaction mixture by distillation under reduced pressure. Examples of suitable pressures here are those in the range from 0.1 to 50 mbar. As a rule, the benzal chlorides are thereby already obtained in a purity sufficient for further reactions. If appropriate, the benzal chlorides thus separated off can be distilled again, for further purification. This is particularly advantageous if the benzal chlorides initially separated off are contaminated by troublesome amounts of unreacted benzotrichlorides and/or disulphides formed from the thiols, which may be the case if the boiling points of the benzotrichloride employed, the benzal chloride formed and/or the disulphide formed are close to one another.

The disulphides, which in general remain in the distillation residue, can be converted back into the corresponding thiols in a known manner by catalytic hydrogenation, and these can then be used again in the reaction according to the invention.

The process according to the invention permits the preparation of the most diverse benzal chlorides from the corresponding benzotrichlorides in a simple manner and with good yields. It is decidedly surprising that if the formation of diphenylethane derivatives occurs at all, it is only to a very minor degree. Traces of diphenylethane derivatives may be formed, the maximum being 2%. The advantages of the process according to the invention are most pronounced if thiophenol is employed as the thiol and copper-I bromide is employed as the metal salt.

The examples which follow illustrate the process according to the invention, without restricting it.

EXAMPLES

Examples 1 to 18

1 mole of the particular benzotrichloride given, 2 moles of thiophenol and 2 g of copper-I bromide were heated under reflux. The evolution of hydrogen chloride started at about 80° C. and the reaction then proceeded slightly exothermically. The temperature was increased slowly to 120° C. and the reaction was brought to completion at 120° C. The benzal chloride obtained in each case was then distilled off from the reaction mixture under reduced pressure. Further details are given in the following table.

| Example No. | Feed material (BTC = benzotrichloride) | Reaction product (BAC = benzal chloride) | Reaction time [hours] | Boiling point [°C.]/pressure [mbar] on distillation | Yield [% of theory] |
| --- | --- | --- | --- | --- | --- |
| 1 | BTC | BAC | 8 | 104–105/30 | 82 |
| 2 | o-Chloro-BTC | o-Chloro-BAC | 8 | 109–110/20 | 76 |
| 3 | p-Chloro-BTC | p-Chloro-BAC | 8 | 120–122/25 | 84 |
| 4 | o,p-Dichloro-BTC | o,p-Dichloro-BAC | 8 | 132–135/20 | 78 |
| 5 | m-Fluoro-BTC | m-Fluoro-BAC | 10 | 94/30 | 72 |
| 6 | p-Fluoro-BTC | p-Fluoro-BAC | 10 | 81–83/20 | 78 |
| 7 | o-Fluoro-o'-chloro-BTC | o-Fluoro-o'-chloro-BAC | 10 | 95/16 | 78 |
| 8 | o,o'-Difluoro-BTC | o,o'-Difluoro-BAC | 10 | 87/20 | 83 |
| 9 | m-Methyl-BTC | m-Methyl-BAC | 8 | 115–117/30 | 58 |
| 10 | o-Trifluoromethyl-BTC | o-Trifluoromethyl-BAC | 10 | 100–102/40 | 75 |

-continued

| Example No. | Feed material (BTC = benzotrichloride) | Reaction product (BAC = benzal chloride) | Reaction time [hours] | Boiling point [°C.]/pressure [mbar] on distillation | Yield [% of theory] |
| --- | --- | --- | --- | --- | --- |
| 11 | m-Trifluoromethyl-BTC | m-Trifluoromethyl-BAC | 10 | 98–99/40 | 95 |
| 12 | p-Trifluoromethyl-BTC | p-Trifluoromethyl-BAC | 10 | 98–100/30 | 89 |
| 13 | m-Trifluoromethoxy-BTC | m-Trifluoromethoxy-BAC | 5 | 103–105/20 | 52 |
| 14 | o-Chloro-m-trifluoromethyl-BTC | o-Chloro-m-trifluoromethyl-BAC | 6 | 106–108/20 | 68 |
| 15 | m-Nitro-m'-trifluoromethyl-p-chloro-BTC | m-Nitro-m'-trifluoromethyl-p-chloro-BAC | 7 | 102–104/0.2 | 72 |
| 16 | o-Cyano-BTC | o-Cyano-BAC | 8 | 155–156/20 (mp.: 37–38) | 95 |
| 17 | m-Cyano-BTC | m-Cyano-BAC | 8 | 158–160/18 | 81 |
| 18 | p-Cyano-BTC | p-Cyano-BAC | 8 | 139–140/18 | 78 |

Example 19 (Reduction with butanethiol)

19.5 g (0.1 mole) of benzotrichloride, 18 g (0.2 mole) of butanethiol and 0.2 g of copper-I bromide were heated to the reflux temperature, while stirring, and were left to react until the evolution of hydrogen chloride had ended (duration: 6 hours). The mixture was then subjected to fractional distillation to give 11.9 g (74%) of benzal chloride at a boiling point of 102°–106° C./30 mbar.

Example 20 (Reduction with thiophenol and Fe(CO)$_5$ as the catalyst)

19.5 g (0.1 mole) of benzotrichloride, 22 g (0.2 mole) of thiophenol and 1 g of iron pentacarbonyl were heated to 120° C. under an inert gas atmosphere of nitrogen, and were left to react until the evolution of hydrogen chloride had ended (duration: 2 hours). 4 g (24%) of benzal chloride were then separated off from the mixture by fractional distillation at a boiling point of 103°–104° C./30 mbar.

Example 21 (Reduction with thiophenol and CuBr in toluene)

19.5 g (0.1 mole) of benzotrichloride, 22 g (0.2 mole) of thiophenol and 0.2 g of copper-I bromide in 40 ml of toluene were slowly heated and were left to react at 120° C. (oil bath temperature) until the evolution of gas had ended (duration: 10 hours). After the solvent had been distilled off, 12.7 g (79%) of benzal chloride were distilled off from the reaction mixture at a boiling point of 100°–104° C./30 mbar.

What is claimed is:

1. A process for preparing a benzal chloride which comprises contacting a benzotrichloride with a thiol in the presence of a halide of copper.

2. A process according to claim 1, wherein the benzotrichloride is one of the formula

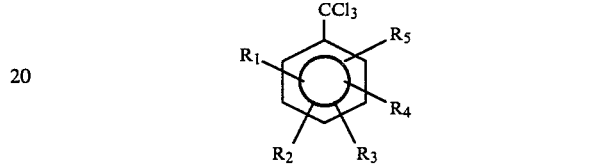

in which

R$_1$ to R$_5$ independently of one another represent hydrogen, nitro, halogen, alkyl, fluoroalkyl, aryl, substituted aryl, O-alkyl, O-fluoroalkyl, phenoxy, substituted phenoxy and/or cyanide, is used.

3. A process according to claim 1 wherein benzotrichloride is one of the formula

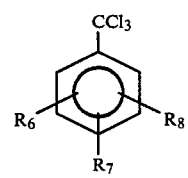

in which

R$_6$ to R$_8$ independently of one another represent hydrogen, nitro, fluorine, chlorine, cyanide, C$_1$–C$_4$-alkyl, C$_1$–C$_4$-fluoroalkyl and/or O-C$_1$–C$_4$-fluoroalkyl, is used.

4. A process according to claim 1, wherein at least 2 moles of thiol are employed per mole of benzotrichloride.

5. A process according to claim 1, wherein the thiol is an aliphatic thiol of 4 to 10 carbon atoms or an aromatic thiol of 6 to 8 carbon atoms.

6. A process according to claim 1, wherein said thiol is thiophenol.

7. A process according to claim 1, wherein said halide of copper is present in the reaction mixture in an amount of 0.01 to 10% by weight, based on the benzotrichloride employed.

8. A process according to claim 1, wherein the reaction is conducted at a temperature between the temperature at which hydrogen chloride commences to evolve and a temperature at which the reaction mixture boils under reflux.

9. A process according to claim 1, wherein the thiol is butane thiol.

10. A process according to claim 2, wherein benzotrichloride is reacted.

11. A process according to claim 1 wherein said halide of copper is copper I bromide.

* * * * *